United States Patent [19]

Sawamura et al.

[11] 4,090,921

[45] May 23, 1978

[54] AUTOMATIC CULTIVATING APPARATUS

[75] Inventors: Ichiro Sawamura; Shinroku Sogi, both of Hachiouji; Shin-ichi Kamachi, Hino; Makoto Yoshinaga, Hachiouji; Atsuo Goto, Tachikawa; Masao Izawa, Hachiouji; Yoshio Nakajima, Hachiouji; Nagahiro Gocho, Hachiouji; Toshio Shinohara, Choufu; Shin-ichiro Hattori, Takamatsu, all of Japan

[73] Assignee: Olympus Optical Co., Ltd., Japan

[21] Appl. No.: 707,068

[22] Filed: Jul. 20, 1976

[30] Foreign Application Priority Data

Jul. 22, 1975 Japan .................................. 50-89315

[51] Int. Cl.$^2$ ............................................. C12K 1/10
[52] U.S. Cl. ..................................... 195/127; 195/142
[58] Field of Search ................ 195/127, 142, 139, 143

[56] References Cited

U.S. PATENT DOCUMENTS

| | | | |
|---|---|---|---|
| 2,975,553 | 3/1961 | Paul | 195/143 |
| 3,172,235 | 3/1965 | Bjorklund | 195/142 |
| 3,437,447 | 4/1969 | Harmon | 195/127 |
| 3,728,227 | 4/1973 | Elson et al. | 195/142 |
| 3,772,154 | 11/1973 | Isenberg et al. | 195/127 |
| 3,844,896 | 10/1974 | Sharpe | 195/139 |
| 3,847,749 | 11/1974 | Smith et al. | 195/127 |
| 3,887,436 | 6/1975 | Haddad et al. | 195/127 |

*Primary Examiner*—Alvin E. Tanenholtz
*Attorney, Agent, or Firm*—Cushman, Darby & Cushman

[57] ABSTRACT

An apparatus for automatically cultivating tissues or cells of a living body comprises a main body the inside of which is maintained in a predetermined atmosphere by an atmosphere control means. A container containing the tissues or cells and a nutrient solution is disposed in the main body and cultivated or multiplied tissues or cells in the container divided and fed for subculture into a plurality of empty cultivating containers disposed in the main body by an operating means which performs necessary operations for subculture. The atmosphere control means and the operating means are totally controlled by an apparatus control means.

7 Claims, 7 Drawing Figures

AUTOMATIC CULTIVATING APPARATUS

BACKGROUND OF THE INVENTION a. Field of the Invention

The present invention relates to an apparatus for automatically cultivating tissues or cells of a living body, and more particularly to such apparatus capable of performing automatically and successively necessary works for subculture of such tissues or cells under predetermined controlled conditions.

b. Description of the Prior Art

In the present instance, techniques for the culture of such tissues, especially cells of a living body have been of fundamental importance in many fields such as medicine, biology and related fields. Due to the technical difficulty of subculture of the tissues of cells of the living body, especially of a human body, stable cultivated "mass" of such tissues or cells could not be obtained until the technique for cultivating such tissues or cells in a gas-sealed incubator was developed. The tissue or cell culture technique in the gas-sealed incubator is a technique to cultivate tissues or cells of a living body in a predetermined gaseous atmosphere. Thanks to this culture technique, it has become possible to cultivate even the distinctive cells of the human body such as liver cells, nervous cells and hypophysis cells.

Conventional subculture of the tissues or cells of the living body has been performed in the following manner. The cells are diluted first by a nutrient solution so that they float in the nutrient solution. A predetermined number of the cells, together with the nutrient solution, are then put into a container such as a Petri dish. The container containing the predetermined number of the cells and the nutrient solution is disposed in an incubator, the inside of which is maintained in a predetermined gaseous atmosphere. In order to check the multiplication state of the cells in the container, the container is take out from within the incubator after predetermined periods of time have passed, and the multiplication state of the cells is inspected by using a microscope. If it is confirmed by such inspection or observation that the cells in the container have multiplied sufficiently enough so that the container has been filled with the multiplied cells, the container is moved to a clean bench in order to divide the multiplied cells into pieces for further subculture. From within the container in the clean bench the nutrient solution in the container is sucked out of the container by means of a pipet. The multiplied cells left in the container are then rinsed by a buffer solution which is injected in the container and the buffer solution is pipetted out of the container after such rinse. After the cleaning of the cells, an enzyme solution such as trypsin is injected into the container in order to make the multiplied cells that are adhered to the inner bottom surface of the container come off and to divide the cells into pieces. The cells are then separated from the enzyme solution by a centrifugal machine and collected. That is, the cells and enzyme solution in the container are transfussed into a tube of the centrifugal machine so as to be separated from each other, and then the enzyme solution in the tube which exists above the cells is sucked out of the tube. It may not be necessary for some kinds of cells to use the centrifugal machine for the purpose of separating the cells and the enzyme solution from each other. In this case, the enzyme solution is sucked out of the container immediately before the adhered cells are liberated by the enzyme solution and the cells are subjected to the next process.

After the enzyme solution has been sucked out of the tube of the centrifugal machine, a fresh nutrient solution is charged into the tube so that the cells in the tube are diluted in the predetermined density of dilution, and this nutrient solution containing the cells divided into pieces float is distributed into empty containers of a predetermined quantity. The container which contains a predetermined number of cells and nutrient solution is then disposed in the incubator, the inside of which is maintained at a predetermined atmosphere, so that the cells in the container are again cultivated.

However, the conventional cultivating manner described hereinbefore has the following disadvantages. One of such disadvantages is that the cultivating container must be often taken out from within the incubator into the air in order to check the multiplication state of the tissues or cells by using the microscope. Therefore, the environment for the culture i.e. gaseous atmosphere, temperature and humidity is greatly changed every time the container is taken out from within the incubator into the air, and this environmental change often causes subtle variations or changes in the tissues or cells in the container. In addition to this drawback, the tissues or cells in the container are contaminated by bacteria or germs contained in the air.

Furthermore, since the necessary operations for subculture, i.e. separating the cells from the enzyme solution, collecting the cells, diluting the cells by the nutrient solution, charging the cells and nutrient solution into the empty container and etc., are munually performed within the clean bench by a skilled technician in accordance with the results of the observation by the microscope, the property of characteristics of the cultivated cells are directly affected by the technician's ability. That is, the property or characteristics of the cultivated tissues or cells depend on the experience and skill of the technician.

Therefore, it is impossible by the conventional cultivating manner to obtain a unified or standardized cultivated tissues or cells.

As the result of the fact that the standardization or unification of the cell culture is very difficult for the reasons described above, opposite conclusions are sometimes obtained by different scientists who have respectively studied the same theme. Thus, the scientist must spare his considerable energies for the cell culture which is not his essential work, instead of devoting his energies to his original medical or biological studies. This is a common worry among the scientists of various fields, and thus the unification or standardization of the tissue or cell culture has been highly desired

SUMMARY OF THE INVENTION

Therefore, it is a primary object of the present invention to provide an apparatus for cultivating tissues or cells of a living body, with which the standardized cultivated tissues or cells can be obtained automatically and successively without any contamination by bacteria or germs and any pollution due to the manual operation.

Another object of the present invention is to provide an apparatus for cultivating tissues or cells of a living body, which enables the necessary operations for subculture to be unified and standardized.

BRIEF DESCRIPTION OF THE DRAWINGS

Other objects and features of the present invention will become apparent to those skilled in the art as the disclosure is made in the following description of a preferred embodiment of the invention, as illustrated in the accompanying drawings and wherein.

DESCRIPTION OF THE PREFERRED EMBODIMENT

Figure 1:
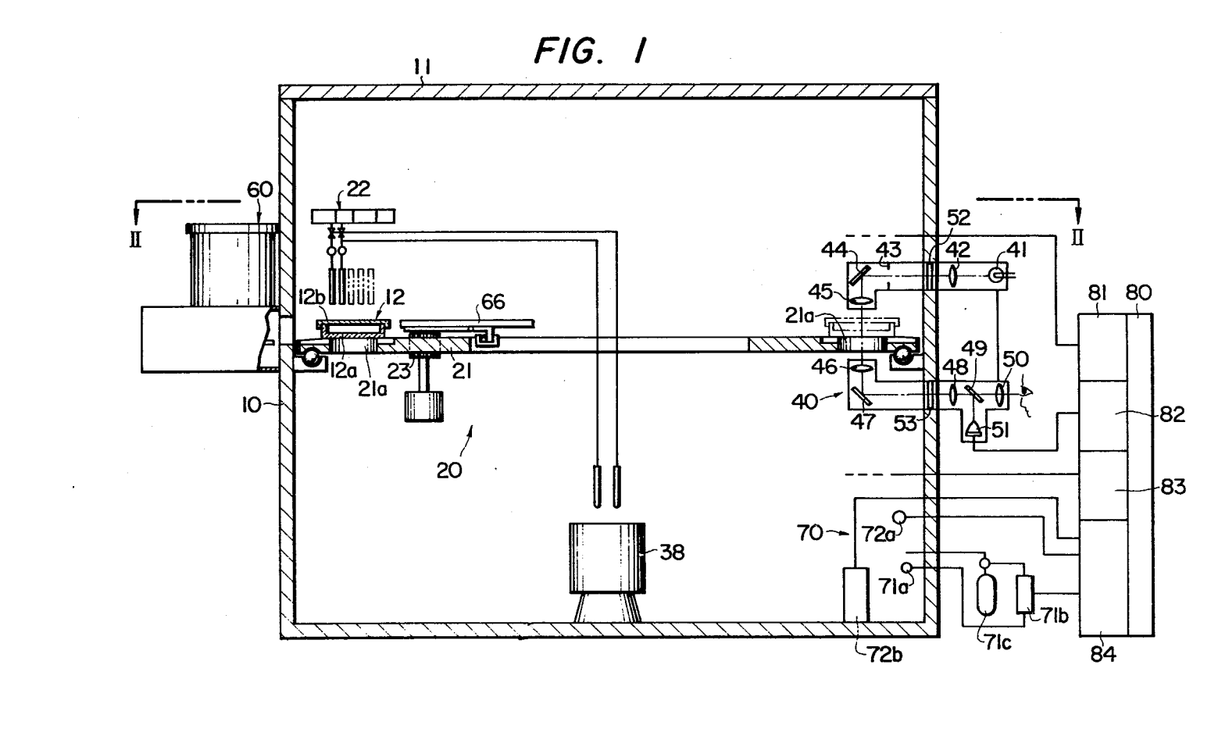
FIG. 1 shows schematically an embodiment of an automatic cultivating apparatus according to the present invention.
Figure 2:
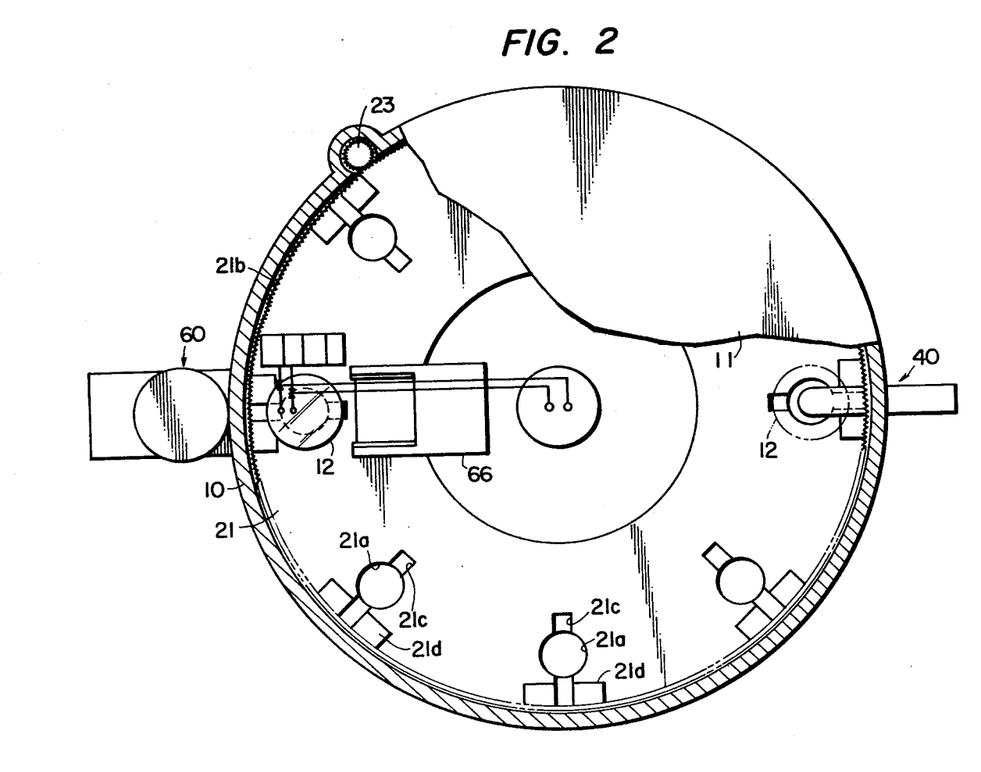
FIG. 2 shows a partially sectional view taken along the lines II—II of FIG. 1.

Referring now to FIGS. 1 and 2, reference numeral 10 designates a main body of the apparatus according to the present invention and reference numeral 11 designates a lid of the main body 10. Reference numeral 12 designates a cultivating container such as a Petri dish, which comprises a container main body 12a and a container lid 12b. The inside of the main body 10 is completely isolated from the air and is maintained in a predetermined atmosphere needed for subculture of tissues or cells of a living body. Disposed in the main body 10 are an operating means 20 for performing necessary works for subculture such as separating the multiplied cells, collecting the cells, diluting the cells and injecting the cells together with a nutrient solution into the empty cultivating containers 12, an inspecting means 40, a container supply means 60 and an atmosphere control means 70. Reference numeral 80 designates an apparatus control means 80 which controls totally the operating means 20, inspecting means 40, container supply means 60 and atmosphere control means 70. The apparatus control means 80 is constituted from a valve control portion 81, an inspection-and-control portion 82, a drive control portion 83 and an atmosphere control portion 84 and each of these control portions 81 through 84 is electrically connected to the related means in the main body 10.

The operating means 20 is constituted from a container carrier board 21 of a disk-like shape and an operating portion 22 which performs necessary operations for subculture of the tissues or cells. As is apparent from FIG. 2, the container carrier board 21 provides a plurality of circular holes 21a at the positions where the cultivating containers are to be placed, and also provides gear teeth 21b around the periphery of the container carrier board 21. A pinion 23 connected to a suitable drive means such as a motor is arranged in the main body 10 so that the pinion 23 can be in meshing engagement with the gear teeth 21b. Thus the container carrier board 21 is rotated by the pinion 23 when the latter is rotated by the suitable drive means.

Figure 3:
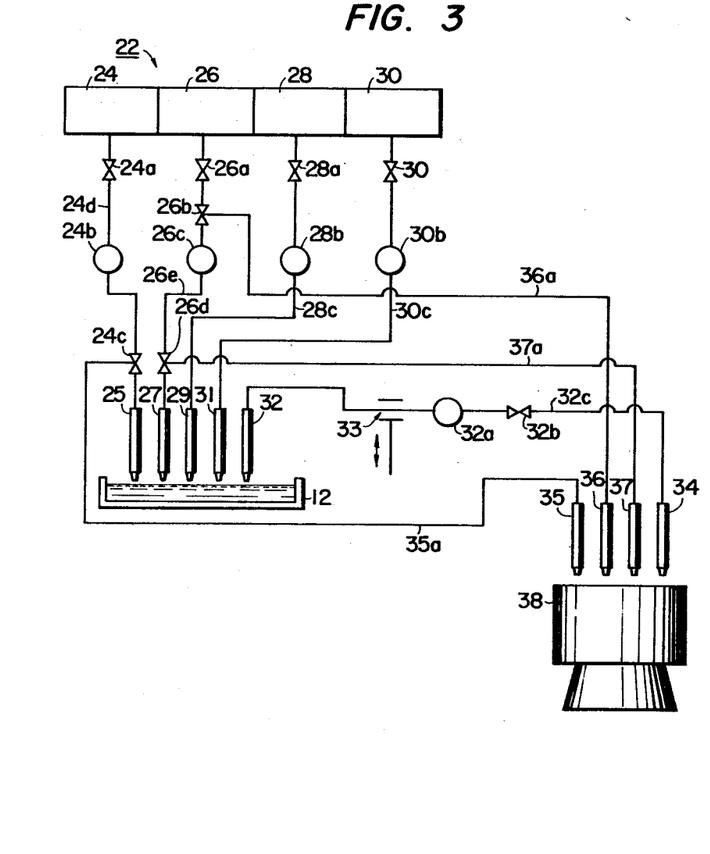
FIG. 3 shows schematically and diagramatically an arrangement of a means for performing necessary operations for subculture such as separating cells, collecting cells and transfusing cells together with a nutrient solution into an empty cultivating container.

The operating portion 22 is shown in more detail in FIG. 3. In FIG. 3, reference numeral 24 designates a discharge trough which is connected by a tube 24d to a discharge nozzle 25 through a valve 24a, a pump 24b and a three-way valve 24c. Reference numeral 26 designates a nutrient solution trough which is similarly connected by a tube 26e to a first nutrient solution charge nozzle 27 through a valve 26a, a three-way valve 26b, a pump 26c and another three-way valve 26d. Reference numeral 28 designates a buffer solution trough which is connected by a tube 28c to a buffer solution charge nozzle 29 through a valve 28a and a pump 28b. Reference numeral 30 designates an enzyme solution trough which is connected by a tube 30c to an enzyme solution charge nozzle 31 through a valve 30a and a pump 30b. Reference numeral 32 designates an agitation nozzle which is connected by a tube 32c to a cell-floating solution charge nozzle 34 through an agitating means 33, a pump 32a and a valve 32b. In this embodiment, the tube 32c may be an elastic tube and the agitating means 33 may be a reciprocating rod having at its one end a pushing plate, which can move back and forth with respect to a suitable stationary member so that the elastic tube 32c placed between the stationary member and the pushing plate is pushed flat when the rod moves in one direction. Due to the elasticity, the tube 32c can return to its original shape from the deformed flat shape when the pushing rod moves back. Reference numeral 35 designates a second discharge nozzle connected to the three-way valve 24c by a tube 35a. Reference numeral 36 designates a suction nozzle connected to the three-way valve 26b by a tube 36a. Reference numeral 37 designates a second nutrient solution charge nozzle which is connected by a tube 37a to the three-way valve 26d, and thus the second nutrient solution charge nozzle 37 is communicatable with the nutrient solution trough 26. These four nozzles i.e. the cell-floating solution charge nozzle 34, the second discharge nozzle 35, the suction nozzle 36 and the second nutrient solution charge nozzle 37 are movably disposed above a centrifugal machine 38 which is used for separating and collecting tissues or cells. In order that the centrifugal machine 38 does not give oscillation to the various parts of the apparatus when the former operates, a suitable buffer mechanism such as a buffer spring (not shown) for absorbing such oscillations is assembled between the main body 10 and the centrifugal machine 38.

The operating means 20 and the operating portion 22 performs necessary works for subculture such as separating cells, collecting cells, diluting cells and transfusing cells together with the nutrient solution into empty cultivating containers, in the manner described hereinafter.

Tissues or cells to be cultivated are put into a cultivating container 12 together with the nutrient solution. The container 12 is then placed on the container carrier board at the position where the circular hole 21a is formed. The main body is isolated from the air by putting the lid 11 on the main body 10 and then is maintained in the predetermined gaseous atmosphere so that the tissues or cells in the container 12 multiply gradually as time passes. After certain periods of time have passed and when it is confirmed by the observation with a microscope that the number of the multiplied cells has reached the predetermined value, the first discharge nozzle 25 is downwardly moved into the container 12 in which the multiplied tissues or cells and the nutrient solution are contained and the nutrient solution is discharged from the container 12 into the discharge trough by opening the valve 24a and by operating the pump 24b. After the nutrient solution has been discharged completely from the container 12, the first discharge nozzle 25 is upwardly moved out of the container 12, the valve 24a is closed and the operation of the pump is stopped. Then the buffer solution charge nozzle 29 is downwardly moved into the container 12 and the buffer solution stored in the buffer solution trough 28 is transfused through the nozzle 29 into the container in the predetermined quantity by opening the valve 28a and operating the pump 28b, so that the surface of the cultivated or multiplied cells is rinsed and cleaned. Subsequent to such rinse, the buffer solution charge nozzle 29 is upwardly moved out of the container 12, the valve 28a is closed and operation of the pump 28b is stopped. The buffer solution used for rinsing or cleaning the cultivated cells is then discharged from the container 12 into the discharge trough 24 by the operation of the valve 24a, the pump 24b and the first discharge nozzle 25 in the same manner described already. After the completion of such discharge of the buffer solution, the enzyme solution charge nozzle 31 is downwardly moved into the container 12 and the enzyme solution stored in the enzyme solution trough 30 is transfused through the nozzle 31 into the container by opening the valve 30a and operating the pump 30b. The enzyme solution charge nozzle 31 is then moved upwardly out of the container 12 immediately after the predetermined quantity of the enzyme solution has been transfused into the container 12. Subsequent to the extraction of the enzyme solution charge nozzle 31, the agitating nozzle 32 is moved downwardly into the container and the pump 32a is simultaneously operated with the valve 32b being closed so that the enzyme solution sucked from the container 12 fills the elastic tube 32c between the nozzle 32 and the valve 32b. When the elastic tube 32c between the nozzle 32 and the valve 32b is filled with the enzyme solution, the operation of the pump 32a is stopped and, at the same time, the agitating means is operated. By the forward movement of the pushing rod of the agitating means, the enzyme solution within the elastic tube 32c is violently pushed out into the container 12 and then sucked into the elastic tube 32c again due to the variation of the pressure within the tube 32c when the pushing rod moves back. Since this operation is continued during the operation of the agitating means 33, the enzyme solution in the container 12 is agitated or stirred. The multiplied cells which adhere to the inner surface of the container are liberated by the agitated enzyme solution and divided into pieces by the function of the enzyme solution. The agitating means is stopped when the cells are divided into pieces, and the enzyme solution containing the liberated or divided cells i.e. a cell-floating solution in the container is sucked through the agitating nozzle 32 into the tube 32c and injected through the cell-floating solution charge nozzle 34 into the centrifugal tube (not shown) of the centrifugal machine by opening the valve 32b and operating the pump 32a. By the operation of the centrifugal machine 38, the cells are separated from the enzyme solution and collected in the lower portion of the centrifugal tube. The enzyme solution from which the cells are extracted and which exists above the collected cells within the centrifugal tube is discharged from the centrifugal tube into the discharge trough 24 by opening the valve 24a, operating the pump 24b and changing over the three-way valve 24c so that the tube 35a and the second discharge nozzle 35 communicate with the tube 24d. After the completion of the discharge of the enzyme solution in the centrifugal tube of the centrifugal machine, the valve 24a is closed and the operation of the pump 24b is stopped. Then the fresh nutrient solution is transfused from the nutrient solution trough 26 through the second nutrient solution charge nozzle 37 by operating the pump 26c after the valve 26a is opened and the three-way valve 26d is changed over so that the nutrient solution trough 26 communicates with the second nutrient solution charge nozzle 37. Thus the cells and the nutrient solution are mixed with each other in the centrifugal tube. The cells and the nutrient solution are then transfused for further subculture of the cells in the predetermined quantity from the centrifugal tube into a plurality of empty cultivating containers successively placed below the first nutrient solution charge valve 27, by changing over the three-way valve 26b so that the suction nozzle 36 communicates with the first nutrient solution charge nozzle 27 and operating the pump 26c. The various operations of the operating means 20 and the operating portion 22 are performed under the total control of the apparatus control means 80. That is, the opening and closing of the valves and the changing over of the three-way valves are controlled by the valve control portion 81, and the operation of each mechanism in the operating means 20 and the operating portion 22, such as the rotation of the container carrier board, is controlled by the drive control portion 83 of the apparatus control means 80.

As is apparent from the foregoing description, it is necessary for the nozzle to be inserted into the cultivating container 12 when, for example, the buffer solution should be transfused from the buffer solution trough 28 into the container 12 or the used nutrient solution and the buffer solution should be discharged from the container 12 into the discharge trough 24. On the other hand, it is preferable to keep the nozzles positioned above the container 12 while the charging or discharging operation is not performed, due to the fact that the container must be moved from the position below the nozzles and that the container lid should be put on the container main body during the culture. For this purpose, it is preferable to provide each nozzle with a suitable drive mechanism comprising, for example, a pinion, rack and/or cams so that only a necessary nozzle is moved independently in the downward and upward directions. However, it is not preferable to arranged the nozzles to be moved together by a single drive mechanism, because the residual solutions at the extreme ends of the nozzles may be touched with the cells. The same thing can be said with respect to the nozzles disposed above the centrifugal machine 38.

Moreover, it is more preferable to clean the nozzles after each operation thereof in order to avoid the contamination and the mixture of the solutions.

It is needless to say that a different type of agitating means may be used as an alternative to the one shown schematically in FIG. 3 and described before.

Now the description will be made to the inspecting means 40. Referring to FIG. 1 again, reference numeral 41 designates a illuminating lamp, reference numeral 42 designates a collector lens, reference numeral 43 designates a bright control means, reference numeral 44 designates a reflecting mirror, reference numeral 45 designates a condenser lens, reference numeral 46 designates an objective lens, reference numeral 47 designates another reflecting mirror, reference numeral 48 designates a relay lens, reference numeral 49 designates a half-mirror, reference numeral 50 designates an eye lens and reference numeral 51 designates inspecting means. Furthermore, reference numerals 52 and 53 respectively designate glass plates disposed in the wall of the main body 10. The condenser lens 45 and the objective lens 46 of the inspecting means 40 are respectively positioned above and below the container carrier board 21 so that their common optical axis can pass through each circular hole 21a when the container carrier board 21 is rotationally moved. Therefore, if it is intended to observe the cells in the cultivating container 12, the container carrier board 21 is rotated into the position where the optical path of the inspecting means 40 passes through the cultivating container 12 containing the cells, and both the observation through the eye lens with the naked-eye and the inspection by the inspecting means are performed. Though the illuminating lamp 41 and the collector lens 42 are disposed outside the main body 10 in the embodiment shown in FIGS. 1 and 2, these elements or parts may be disposed within the main body 10.

Figure 4:
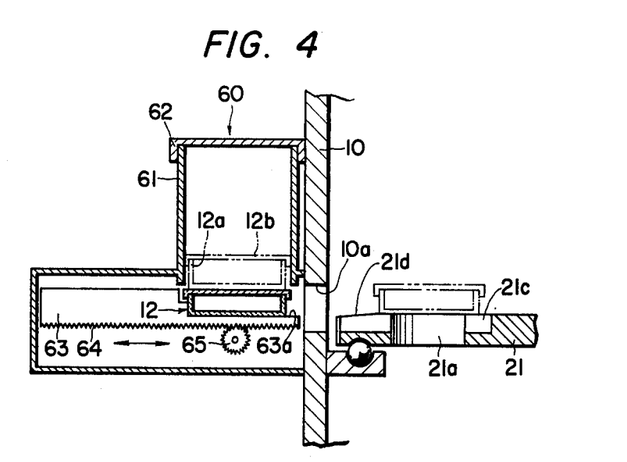
FIG. 4 shows schematically a sectional view of a container supply means for use in the apparatus shown in FIG. 1.

The container supply means 60 is arranged as shown in FIG. 4. In FIG. 4, reference numeral 61 designates a container store chamber with a chamber lid 62 and reference numeral 63 designates a container supply member provided with a rack 64 at the lower surface thereof. The container supply member 63 is supported in the chamber 61 so as to move in the horizontal direction. Reference numeral 65 designates a pinion adapted to be meshed with the rack 64 of the container supply member 63. The pinion 65 is coupled to a suitable drive means such as a motor (not shown). The container store chamber 61 is also isolated from the air and communicates with the inside of the main body through a window 10a which is formed in the wall of the main body 10. The cultivating container stored in the container store chamber 61 in stacked condition are transported one by one from the chamber 61 onto the container carrier board by the container supply member 63. That is, the container supply member 63 is moved in the rightward direction by the pinion 65 and thus the lowermost container on the container supply member 63 is pushed out from the chamber 61 into the main body 10 through the window 10a. In this embodiment, as shown in FIGS. 1 through 3, elongated slots 21c which extend from the periphery of the container carrier board 21 toward the center thereof through respective circular holes 21a are formed in the container carrier board 21, and inclined portions 21d are also formed between respective circular holes 21a and the periphery of the container carrier board 21. Therefore, the cultivating container 12 introduced into the main body 10 through the window 10a is pushed on the container carrier board 21 through the inclined portion 21d by the container supply member 63 if the container carrier board 21 is brought into the position where the container supply member 63 and one of the elongated slots 21c are aligned with each other. In this case, the container supply member 63 advances in the elongated slot 21c. Therefore, if the container carrier board 21 is returned to its original position shown in FIG. 4 by the reversal of the pinion 65, the container 12 is left on the container carrier board 21 at the predetermined position above the circular hole 21a. Since the next lowermost container 12 is put on the container supply member 63 when the latter returns to its original position, the stacked cultivating containers 12 in the chamber 61 are successively transported onto the container carrier board 21 by repeating the same operation as described above.

Figure 5A:
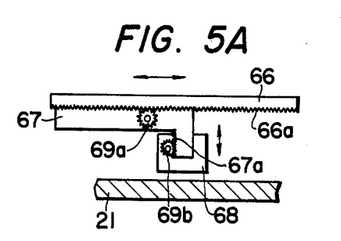
FIG. 5A shows schematically a front view of a lid removing means for removing a lid of a cultivating container within the apparatus shown in FIG. 1.
Figure 5B:
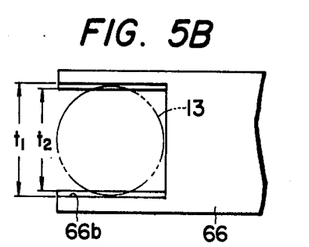
FIG. 5B shows a partial, top plan view of a lid removing plate of the lid removing means shown in FIG. 5A.
Figure 5C:
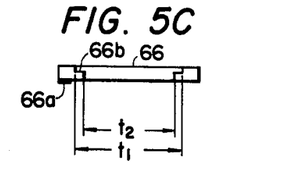
FIG. 5C shows a side view of the lid removing plate shown in FIG. 5B.

In order to inject the cells and the nutrient solution into the cultivating container 12 which is put on the container carrier board 21 by the operation of the container supply member 63, it is necessary to remove the container lid 12b of the cultivating container 12. For this purpose, a lid removing mechanism is provided in the main body. The lid removing mechanism is shown in FIG. 5A and comprises a lid removing member 66. As shown in FIGS. 5B and 5C, one end of the lid removing member 66 is bifurcated and a step portion 66b is formed at the inside of each tine. The distance $t_1$ between both step portions of the tines is selected to be approximately equal to the outer diameter of the container lid 12b of the cultivating container 12 and the distance $t_2$ between both inner surfaces of the tines is selected to be approximately equal to the outer diameter of the container main body 12a of the cultivating container 12. Therefore, if the lid removing member 66 is horizontally advanced toward the cultivating container 12 with shoulders of the step portions 66b being positioned below the lower end surface, the cultivating container 12 may be placed between both tines of the lid removing member 66. In this condition, if the lid removing member 66 is moved upwardly the container lid 12b is carried by the lid removing member 66 leaving the container main body 12a as it is, since the shoulders of the tines of the lid removing member 66 support the container lid 12b. As shown in FIG. 5A, the lid removing member 66 is supported by a support member 67 so as to move only in the horizontal direction with respect to the support member 67. A pinion 69a coupled to a suitable drive means (not shown) is supported by the support member 67 so that the pinion 69a can be in meshing engagement with a rack 66a formed on the lower surface of the lid removing member 66. The support member 67 comprises a vertical rack 67a and is supported by the main body by a suitable support means (not shown) so as to move only in the vertical direction. Another support member 68 fixed to the suitable support means is disposed below the first support member 67. Another pinion 69b coupled to a suitable drive means (not shown) is supported by the second support member 68 so that the pinion 69b can be in meshing engagement with the vertical rack 67a of the first support member 67. Therefore, the lid removing member 66 can be moved horizontally by the rotation of the pinion 69a and vertically by the rotation of the pinion 69b.

The lid removing mechanism shown in FIG. 5A is disposed in the main body 10 so as to be opposite to the container supply means 60, as shown in FIGS. 1 and 2. For example, in the case of the charging of the cells and the nutrient solution into the empty cultivating container 12, the container 12 is placed first on the predetermined position of the container carrier board 21 by the operation of the container supply member 63. In this case, the lid removing member 66 must be in its lowermost position where a plane including the shoulders of the step portions 66b thereof is in a lower portion than the plane including lower end surface of the container lid 12b of the cultivating container 12 on the container carrier board 21. The lid removing member 66 is then advanced horizontally in the leftward direction in FIG. 1 by the rotation of the pinion 69a until the cultivating container is positioned between the tines of the lid removing member 66. Then the pinion 69b is rotated so as to move the support member 67 together with the lid removing member 66 in the upward direction. By this upward movement of the lid removing member 66, the container lid 12b is supported by the lid removing member 66 through the shoulders thereof and lifted together with the lid removing member 66. The container lid 12b is thus removed from the container main body 12a. The lid removing member is then returned to its first position by the reverse rotation of the pinion 69a so as to permit the insertion of the first nutrient solution charge nozzle 27 into the container main body 12a. The removed container lid 12b can be put again on the corresponding container main body 12a through the reverse steps of the lid removing steps described above. These operations of the container supply means 60 and the lid removing means shown in FIG. 5A, as well as the rotation of the container carrier board 21, are controlled by the drive control portion 83.

The atmosphere control means 70 shown in FIG. 1 comprises a $CO_2$ detector 71a, a $CO_2$ detection-and-control means 71b, a $CO_2$ gas container 71c, a temperature detector 72a and a temperature adjastor 72b. With these members of the atmosphere control means 70, the atmosphere in the main body 10 is maintained in a best condition for subculture under the control of the atmosphere control portion 84 of the apparatus control means 80. Though only the temperature and the $CO_2$ gas control means are shown in FIG. 1, it is needless to say that a humidity, $N_2$ gas and $O_2$ gas control means are assembled to the actual cultivating apparatus and connected to the atmosphere control portion 84 since the inside of the main body 10 must be continuously maintained in the constant temperature and humidity and the constant gaseous atmosphere where the $CO_2$ gas, $N_2$ gas and $O_2$ gas are mixed at the predetermined rate.

It is possible to constitute the arrangement of the apparatus control means 80 as a mere sequence control means. However, if the apparatus control means 80 is connected to a computor through a suitable interface means, the whole operation of the cultivating apparatus according to the invention can be programmably controlled in accordance with a predetermined program.

The total operation of the cultivating apparatus according to the present invention is as follows.

The tissues or cells to be cultivated are put into an empty cultivating container 12 together with the nutrient solution. The cultivating container 12 thus containing the tissues or cells and the nutrient solution is then put on the predetermined position of the container carrier board 20 in the main body 10, the inside of which is maintained in the desired atmosphere, for the certain periods of time until the tissues or cells multiply sufficiently. When inspecting or observing the multiplication state during the culture, the container carrier board is rotated until the container 12 is brought into the position between the condenser lens 45 and the objective lens 46 of the inspecting means 40. The inspection or observation of the tissues or cells can be performed with the naked-eye or by the inspecting means 51. If it is confirmed by such inspection or observation that the container 12 is full of the multiplied cells, the container carrier board is again rotated until the container 12 is brought into the position between the container store chamber 61 and the lid removing mechanism including the lid removing means 66. The container lid 12b of the container 12 is then removed by the operation of the lid removing mechanism. After removing the container lid 12b, necessary operations for making subculture such as discharging the nutrient solution, rinsing the cells by the buffer solution, separating and liberating cells adhered to the container 12 and separating the cells from the enzyme solution by the centrifugal machine are performed in the manner already described making reference to FIG. 3. Subsequent to the completion of these works, the container carrier board 21 is rotated until the subsequent circular hole 21a is brought into the position between the container store chamber 61 and the lid removing mechanism, where the associated slot 21c is aligned with the container supply member 63. Then, a empty new cultivating container 12 is put on the container carrier board 21 by the operation of the container supply member 63. The container lid 12b of the new empty container 12 is then removed by the lid removing mechanism including the lid removing member 66 and the separated cells and the fresh nutrient solution are fed into the empty container 12 for further subculture of the cells after the removed container lid 12b is again put on the container main body 12a. In this manner, several cultivating containers are moved one by one from the container store chamber 61 onto the container carrier board 21 and the cells and the nutrient solution are fed into each one of the containers. That is, the cells cultivated and multiplied in the first cultivating container are divided and fed into the new empty containers together with the fresh nutrient solution for further subculture of the cells.

As the inspecting method for inspecting the multiplication state of the cells in the container 12 by means of the inspecting means 51, various methods such as ones utilizing a spectrum or spectral pattern, an ion detection and a variation of the electric resistance may be used.

Instead of using the container supply means, a plurality of the empty cultivating containers 12 may be previously placed on the container carrier board 21.

What we claim is:

1. An apparatus for automatically cultivating tissues or cells of a living body comprising:
   at least one cultivating container into which the tissues or cells and a nutrient solution are placed, said container having a removable lid;
   a plurality of empty cultivating containers each having a removal lid;
   a main body into which said cultivating container containing the tissues or cells and the nutrient solution and said empty containers are placed, the inside of said main body isolated from the atmosphere;
   a container carrier board mounted in said main body and having a plurality of circular holes near the periphery of said container carrier board for each receiving a container;
   inspecting means comprising an illuminating optical system mounted on one side of said container carrier board and an observing and light-measuring optical system mounted on the other side of said container carrier board, said inspecting means being provided for inspecting the multiplication state of the tissues or cells in said cultivating container by transmitted illumination;
   operating means disposed within said main body and comprising a discharge trough, a nutrient solution trough, a buffer solution trough, and an enzyme solution trough, each respectively connected to a nozzle through tubes, valves and pumps, and a centrifugal machine for receiving the multiplied cells from said cultivating container and separating the multiplied cells from the nutrient solution, said operating means carrying out operations for subculture of the tissues or cells so that the multiplied tissues or cells are divided and fed into each of said empty cultivating containers, together with a fresh nutrient solution;

means for continuously detecting the atmosphere in said main body and maintaining the atmosphere constant, comprising a gas detector, gas control means, temperature detector and temperature adjustor;

control means disposed outside said main body comprising a valve control means, inspection and control means; drive means, and atmosphere detecting means, said control means controlling said inspecting means, operating means and means for continuously maintaining the atmosphere constant;

a container supply means for supplying new empty containers into said main body; and means disposed within said main body for removing said lids from said containers for carrying out said operations and replacing said lids thereafter.

2. An apparatus for automatically cultivating tissues or cells of a living body according to claim 1, in which said container carrier board has gear teeth around its periphery, said apparatus for automatically cultivating tissues or cells of a living body further comprising a pinion meshing with said gear teeth, said container carrier board being intermittently rotated by rotation of said pinion.

3. An apparatus for automatically cultivating tissues or cells of a living body according to claim 1, in which said illuminating optical system comprises an illuminating lamp, collector lens, reflecting mirror and condenser lens, and said observing and light-measuring optical system comprises an objective lens, another reflecting mirror, eyepiece, and photoelectric inspecting means, said illuminating lamp, eyepiece and photoelectric inspecting means being arranged outside said main body.

4. An apparatus for automatically cultivating tissues or cells of a living body according to claim 1, wherein said container supply means includes container storage chamber accommodating a plurality of empty cultivating containers and a container supply member for moving said empty cultivating containers in turn onto said container carrier board through a window formed in said main body.

5. An apparatus for automatically cultivating tissues or cells of a living body according to claim 4, wherein said lid removing means includes a lid removing member, of which one end portion is bifurcated to form two tines each having a step portion formed on the inner side and which is arranged to move in vertical and horizontal directions.

6. An apparatus for automatically cultivating tissues or cells of a living body according to claim 1, wherein said lid removing means includes a lid removing member, for which one end portion is bifurcated to form two tines each having a step portion formed on the inner side and which is arranged to move in vertical and horizontal directions.

7. An apparatus for automatically cultivating tissues or cells of a living body according to claim 6, in which said tines of said lid removing member are formed so that the distance between both step portions of the tines is approximately equal to the outer diameter of the container lid and the distance between both inner surfaces of the tines is approximately equal to the outer diameter of the container main body.

* * * * *